(12) United States Patent
Hurt et al.

(10) Patent No.: US 7,866,493 B1
(45) Date of Patent: Jan. 11, 2011

(54) STORAGE APPARATUS FOR USE IN A HOSPITAL ENVIRONMENT AND ASSOCIATED METHOD

(76) Inventors: Jacqueline Hurt, 5247 Brighton Shore, Apollo Beach, FL (US) 33572; Kim Likens, 570 S. Rainier Dr., St. George, UT (US) 84770

( * ) Notice: Subject to any disclaimer, the term of this patent is extended or adjusted under 35 U.S.C. 154(b) by 500 days.

(21) Appl. No.: 11/986,223

(22) Filed: Nov. 20, 2007

Related U.S. Application Data (60) Provisional application No. 60/859,899, filed on Nov. 20, 2006.

(51) Int. Cl.
*A47G 29/08* (2006.01)

(52) U.S. Cl. .................. 211/119.004; 211/113; 211/85.3

(58) Field of Classification Search .......... 211/119.004, 211/113, 85.2, 85.3, 36, 38, 180; 312/3–6; 206/286; 383/38–40
See application file for complete search history.

(56) References Cited

U.S. PATENT DOCUMENTS

| | | | | |
|---|---|---|---|---|
| 962,595 | A * | 6/1910 | Smith | 211/88.01 |
| 1,684,232 | A * | 9/1928 | Levit | 383/38 |
| 2,441,415 | A * | 5/1948 | Hoishman | 383/39 |
| 2,639,819 | A * | 5/1953 | Marks | 108/164 |
| 2,780,260 | A * | 2/1957 | Watson | 383/23 |
| 2,832,389 | A * | 4/1958 | Smith | 383/9 |
| 3,029,852 | A * | 4/1962 | Taylor | 383/2 |
| 3,181,751 | A * | 5/1965 | Wilson | 383/39 |
| 3,184,273 | A * | 5/1965 | Blough | 312/6 |
| 3,435,868 | A * | 4/1969 | Stermer | 206/455 |
| 3,904,258 | A * | 9/1975 | Faulkenberry | 312/6 |
| 4,301,916 | A * | 11/1981 | Handelman | 206/38 |
| 4,329,789 | A * | 5/1982 | Erickson | 34/195 |
| 4,585,127 | A * | 4/1986 | Benedict | 211/34 |
| 4,736,853 | A * | 4/1988 | O'Mara | 211/88.01 |
| 4,901,899 | A * | 2/1990 | Barrett | 224/223 |
| 4,947,987 | A * | 8/1990 | Keenan | 206/292 |
| 4,953,765 | A * | 9/1990 | Little et al. | 224/583 |
| 4,960,204 | A * | 10/1990 | Young et al. | 206/235 |
| 5,542,530 | A * | 8/1996 | Freelander | 206/292 |
| 5,598,923 | A * | 2/1997 | Owens | 206/370 |
| 5,890,587 | A * | 4/1999 | Roegner | 206/6.1 |
| 5,984,361 | A | 11/1999 | Westerman | |
| 6,030,121 | A * | 2/2000 | Strzyinski et al. | 383/39 |
| 6,209,734 | B1 * | 4/2001 | Wang | 211/87.01 |
| 6,685,023 | B2 * | 2/2004 | Bleggi et al. | 206/493 |
| 6,719,157 | B2 * | 4/2004 | Stoddart et al. | 211/118 |
| 6,729,519 | B2 | 5/2004 | Kestler | |
| 6,732,659 | B2 * | 5/2004 | Poon | 108/42 |
| 6,874,624 | B2 | 4/2005 | Redzisz | |
| 7,165,687 | B1 * | 1/2007 | Stevens et al. | 211/86.01 |
| 7,389,868 | B2 * | 6/2008 | Lewand et al. | 206/6.1 |

(Continued)

*Primary Examiner*—Jennifer E. Novosad (57) ABSTRACT

A portable storage apparatus for holding hospital supplies includes a planar back wall extending along an entire longitudinal length of the storage apparatus and a plurality of storage compartments directly affixed to an anterior surface of the back wall and protruding forwardly therefrom. The apparatus further includes at least one flexible protective shield anchored to the back wall and selectively adapted between raised and lowered positions such that the compartments are exposed and isolated from an ambient region surrounding the storage apparatus. The apparatus further includes a mechanism for hanging the storage apparatus on the door such that the back wall contiguously lays against a planar side of the door and a mechanism for biasing the protective shield to a locked position.

18 Claims, 10 Drawing Sheets

U.S. PATENT DOCUMENTS

| | | | |
|---|---|---|---|
| 2002/0071618 A1* | 6/2002 | Felsenthal | 383/39 |
| 2002/0190017 A1* | 12/2002 | Stevens | 211/118 |
| 2003/0150828 A1* | 8/2003 | Bennett et al. | 211/118 |
| 2004/0140282 A1* | 7/2004 | Wang | 211/113 |
| 2005/0230336 A1* | 10/2005 | Mundy et al. | 211/113 |
| 2006/0049124 A1* | 3/2006 | Wang | 211/113 |
| 2008/0174214 A1* | 7/2008 | Segall et al. | 312/6 |
| 2009/0080808 A1* | 3/2009 | Hagen | 383/12 |

* cited by examiner

STORAGE APPARATUS FOR USE IN A HOSPITAL ENVIRONMENT AND ASSOCIATED METHOD

CROSS REFERENCE TO RELATED APPLICATIONS

This application claims the benefit of U.S. Provisional Application No. 60/859,899, filed Nov. 20, 2006, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to storage apparatuses and, more particularly, to a storage apparatus for holding hospital supplies without blocking doorways or impeding traffic flow.

2. Prior Art

Medical carts have traveled down a long corridor since the days when they were stainless steel footlockers the size of an automobile. The catalyst for change was the professional tool cart used by garage mechanics. In 1970, cart manufacturers saw how the tool cart could be applied to the medical field. From that point on, medical carts became the preeminent mobile storage system for hospitals, and continued to evolve as needs changed. Manufacturers have used user feedback to develop carts that have gone from obese to slender and nimble. Although carts have become smaller and more efficient, they are not without drawbacks, primarily the problem of blocking doorways and preventing escape in the event of a fire or natural disaster. Based on the above mentioned needs, it would be advantageous to provide a means for a convenient and space saving means of storage.

U.S. Pat. No. 5,984,361 to Westerman II discloses sorting and filing of particular items that is achieved using an organizer and a method for organizing. An organizing device has a plurality of pocket enclosures correlating to a specific day of a week or month. Pocket enclosures on each particular date have dimensions sufficient to retain physical items, such as envelopes, bills, etc. as well as additional pockets for miscellaneous materials. The organizing device is designed to hang over a door and may also include appliques to indicate numerals, color codes, appointments, etc. Unfortunately, this prior art example does not include a protective shield for preventing inadvertent access to stored items.

U.S. Pat. No. 6,729,519 to Kestler discloses a laundry backpack, which can be hung from a door, which has a D-shaped perimeter frame in the front and back of the backpack. The laundry backpack has closeable shields in the front, top and bottom. The laundry backpack may have a firm material in the top or bottom for front to back for support. The laundry backpack has a detachable hanging strap with a U-shaped hanger for hanging over a door. Unfortunately, this prior art example does not include a plurality of storage compartments for housing various items.

U.S. Pat. No. 6,874,624 to Redzisz discloses a hanging organizer and storage device that includes a semi-rigid pad or pad sections encapsulated in a fabric material with a circumferential wire reinforcement and a hanging hook construction attached to the top edge of the organizer for suspension from a panel or door. Unfortunately, this prior art example does not include a protective shield for preventing inadvertent access to stored items.

Accordingly, the present invention is disclosed in order to overcome the above noted shortcomings. The present invention is convenient and easy to use, lightweight yet durable in design, and designed for holding hospital supplies without blocking doorways or impeding traffic flow. The storage apparatus is simple to use, inexpensive, and designed for many years of repeated use.

BRIEF SUMMARY OF THE INVENTION

In view of the foregoing background, it is therefore an object of the present invention to provide an apparatus for holding hospital supplies without blocking doorways or impeding traffic flow. These and other objects, features, and advantages of the invention are provided by a storage apparatus.

A portable storage apparatus for holding hospital supplies includes a planar back wall effectively extending along an entire longitudinal length of the storage apparatus and a plurality of storage compartments directly affixed to an anterior surface of the back wall and protruding forwardly therefrom. Each of such storage compartments has a plurality of monolithically formed sides defining a cavity therebetween and is provided with an open top end respectively.

The apparatus further includes at least one flexible protective shield anchored to the back wall and selectively adapted between raised and lowered positions such that the compartments are conveniently exposed and isolated from an ambient region surrounding the storage apparatus. Such a protective shield has a plurality of apertures formed therein which adjoin a bottom most edge thereof. The protective shield is freely adapted between the lowered and raised positions while the back wall maintains direct contact with a door.

The protective shield covers all of the storage compartments and extends downwardly from the back wall to a termination point defined subjacent a bottom-most pair of the storage compartments. The protective shield advantageously extends along a first sloping plane registered generally orthogonal to the back wall and is further seated along selected ones of the top ends of an upper-most pair of the most storage compartments respectively. The protective shield further extends along a second sloping plane effectively registered generally orthogonal to the first sloping plane while seated along an anterior face of the storage compartments respectively.

The apparatus further includes a mechanism for conveniently hanging the storage apparatus on the door such that the back wall contiguously lays against a planar side of the door. Such a hanging mechanism includes a plurality of brackets removably engaged with a top most edge of the door and extending vertically down therefrom. Each of such brackets is coextensively shaped and spaced apart such that outermost ones of the brackets are generally vertically aligned with lateral edges of the back wall. A plurality of eyelets is directly coupled to a top most edge of the back wall and juxtaposed subjacent to the brackets, and a plurality of flexible cords have axially opposed ends anchored to the eyelets and the brackets respectively. Bottom hooked end portions of such brackets advantageously fit through the apertures when the protective shield is lifted to the raised position such that the storage compartments are exposed and freely acceptable by a user.

The apparatus further includes a mechanism for effectively biasing the protective shield to a locked position when adapted to the lowered position such that the protective shield is prohibited from disengaging respective front faces of the storage compartments why disposed at the lowered position. Such a biasing mechanism includes a plurality of fasteners coupled directly to a bottom-most positioned pair of the storage compartments such that the aperture is removably attached directly to the fasteners when the protective shield is unrolled to the lowered position.

A method for storing hospital supplies without blocking doorways or impeding traffic flow includes the steps of: providing a planar back wall extending along an entire longitudinal length of the storage apparatus; directly affixing a plurality of storage compartments to an anterior surface of the back wall by protruding the storage compartments forwardly therefrom, each of the storage compartments has a plurality of monolithically formed sides defining a cavity therebetween and is provided with an open top end respectively; anchoring at least one flexible protective shield to the back wall; hanging the storage apparatus on the door such that the back wall contiguously lays against a planar side of the door; and selectively adapting the protective shield between raised and lowered positions while the back wall maintains direct contact with a door such that the compartments become exposed and isolated from an ambient region surrounding the storage apparatus.

The method further includes the steps of: biasing the protective shield to a locked position when adapted to the lowered position and thereby prohibiting the protective shield from disengaging respective front faces of the storage compartments why disposed at the lowered position; coupling a plurality of fasteners directly to a bottom-most positioned pair of the storage compartments; and removably attaching the fasteners directly to the protective shield by unrolling the protective shield to the lowered position.

The method further includes the steps of: covering all of the storage compartments by extending the protective shield downwardly from the back wall to a termination point defined subjacent a bottom-most pair of the storage compartments; extending the protective shield along a first sloping plane registered generally orthogonal to the back wall by seating the protective shield along selected ones of the top ends of an upper-most pair of the most storage compartments respectively; and further extending the protective shield along a second sloping plane registered generally orthogonal to the first sloping plane by seating the protective shield along an anterior face of the storage compartments respectively.

The method further includes the steps of: removably engaging a plurality of brackets with a top most edge of the door by vertically extending the brackets down therefrom; vertically aligning outermost ones of the brackets generally with lateral edges of the back wall; directly coupling a plurality of eyelets to a top most edge of the back wall by juxtaposing the eyelets subjacent to the brackets; anchoring axially opposed ends of a plurality of flexible cords to the eyelets and the brackets respectively; and fitting bottom hooked end portions of the brackets through the apertures by lifting the protective shield to the raised position and thereby exposing the storage compartments to a user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with, reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-9 by the reference numeral 10 and is intended to protect a storage apparatus for holding hospital supplies. It should be understood that the apparatus 10 may be used to hold many different types of supplies and should not be limited in use with only those types of supplies mentioned herein.

Figure 1:
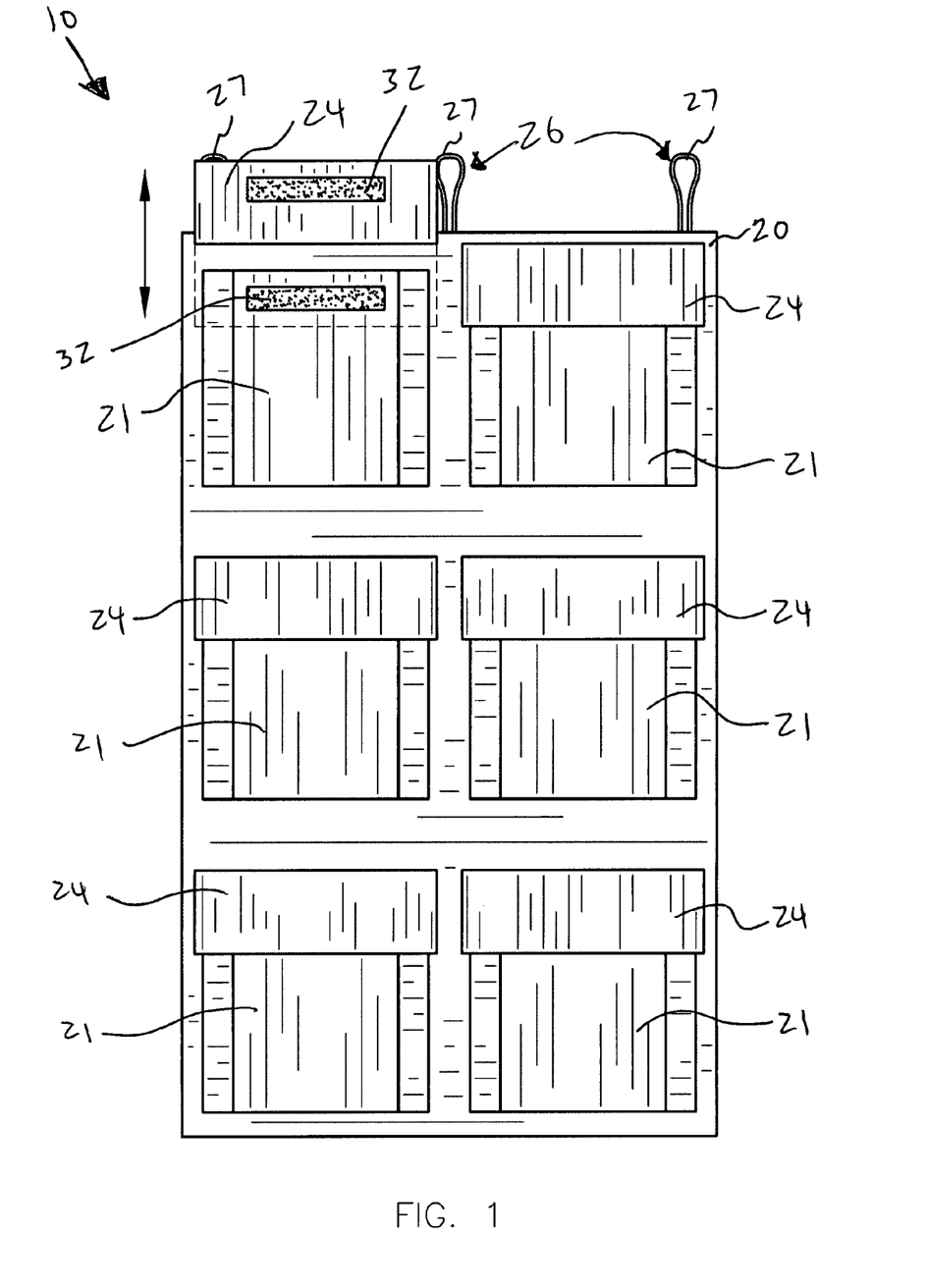
FIG. 1 is a front elevational view showing a plurality of isolated pockets provided with respective VELCRO sealed protective shields, in accordance with a preferred embodiment of the present invention.
Figure 2:
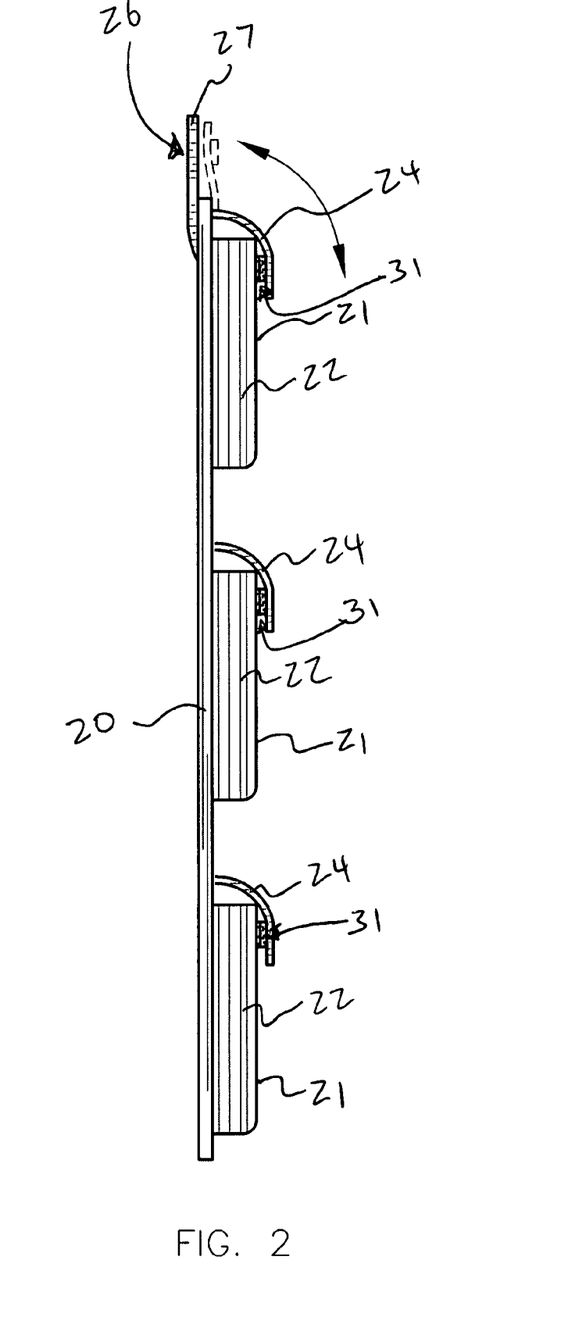
FIG. 2 is a side elevational view of FIG. 1.
Figure 3:
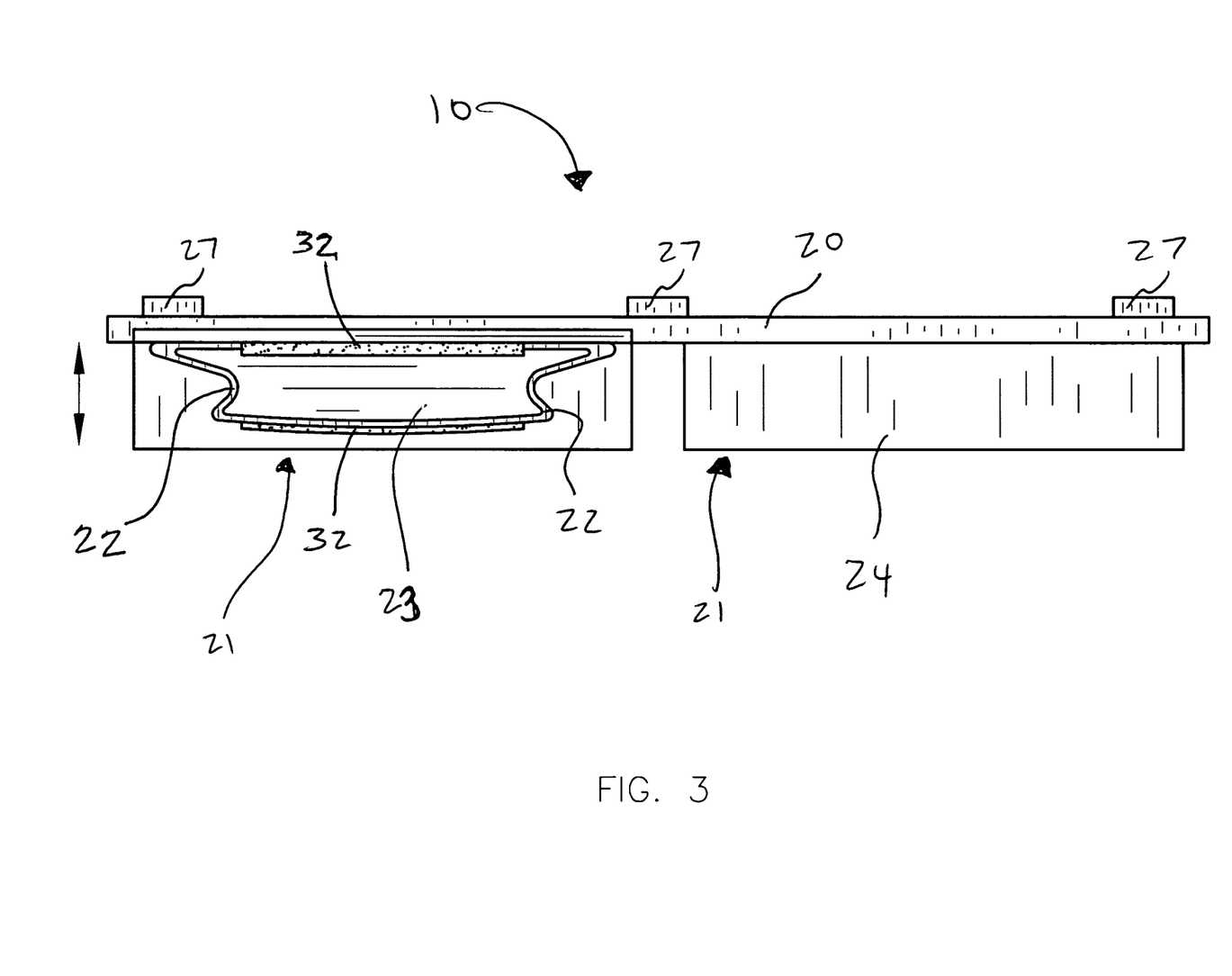
FIG. 3 is top plan view of FIG. 1.
Figure 4:
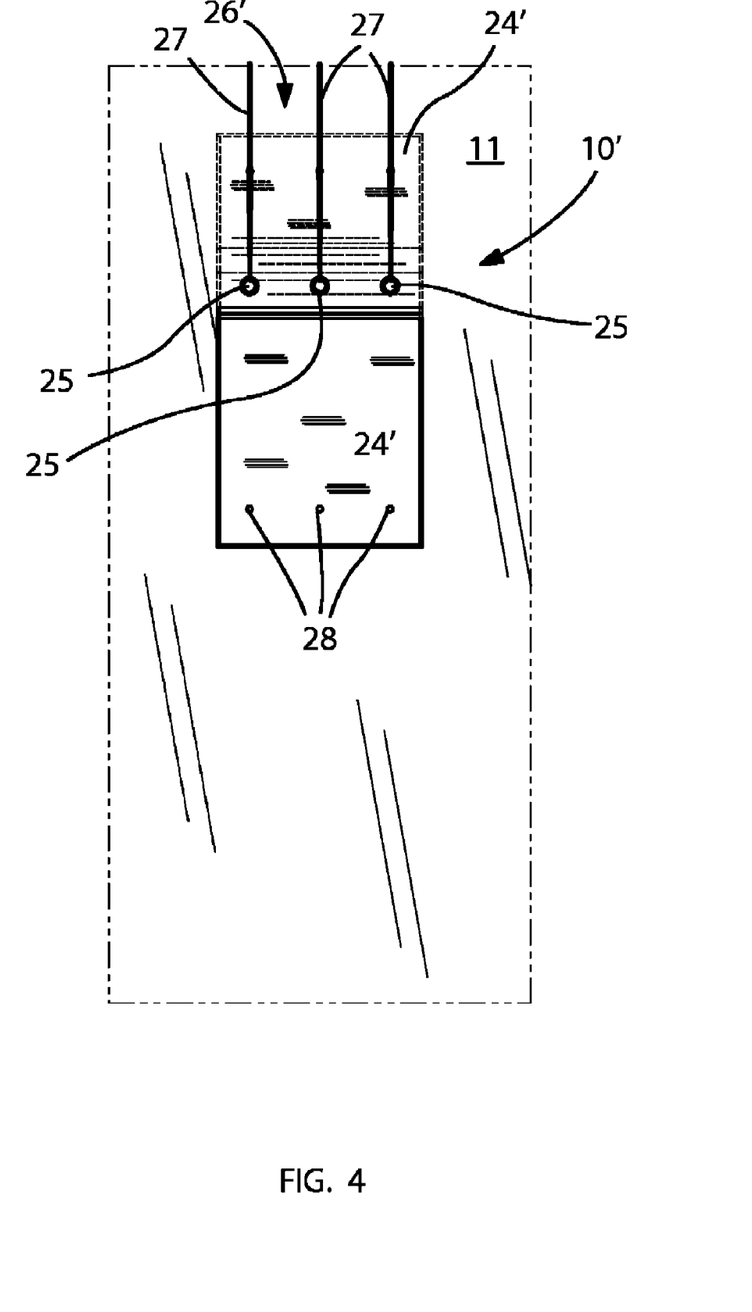
FIG. 4 is a front elevational view of a storage apparatus, in accordance with an alternate embodiment of the present invention.
Figure 5:
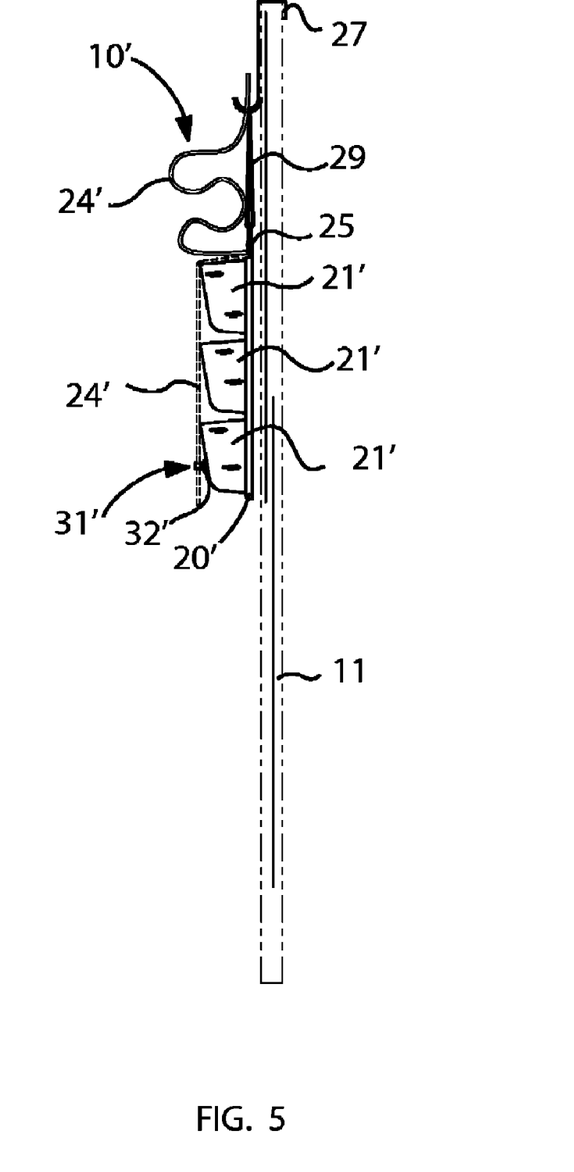
FIG. 5 is a side elevational view of a storage apparatus, in accordance with the embodiment shown in FIG. 4.
Figure 6:
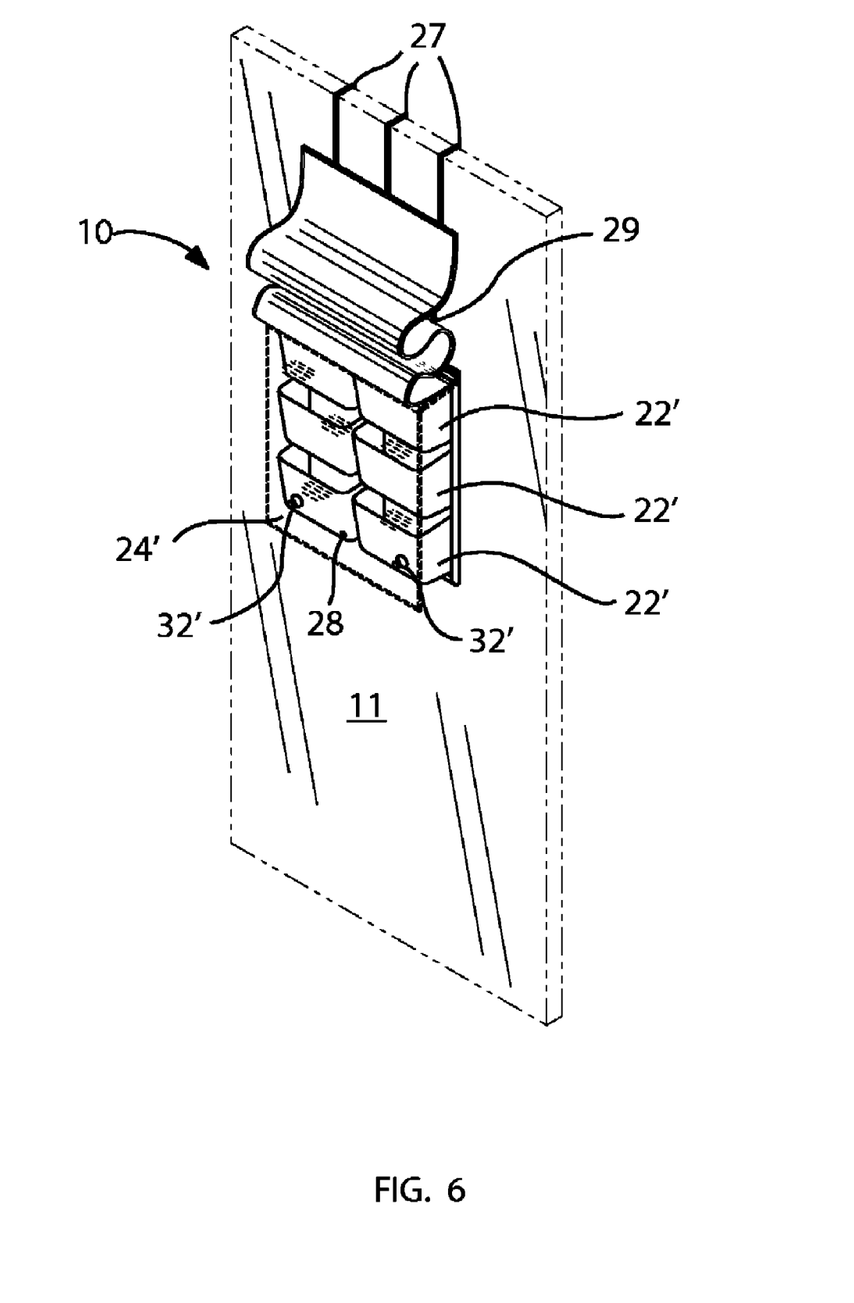
FIG. 6 is a perspective view of a storage apparatus, showing the protective shield in open and closed positions, in accordance with the embodiment shown in FIG. 4.
Figure 7:
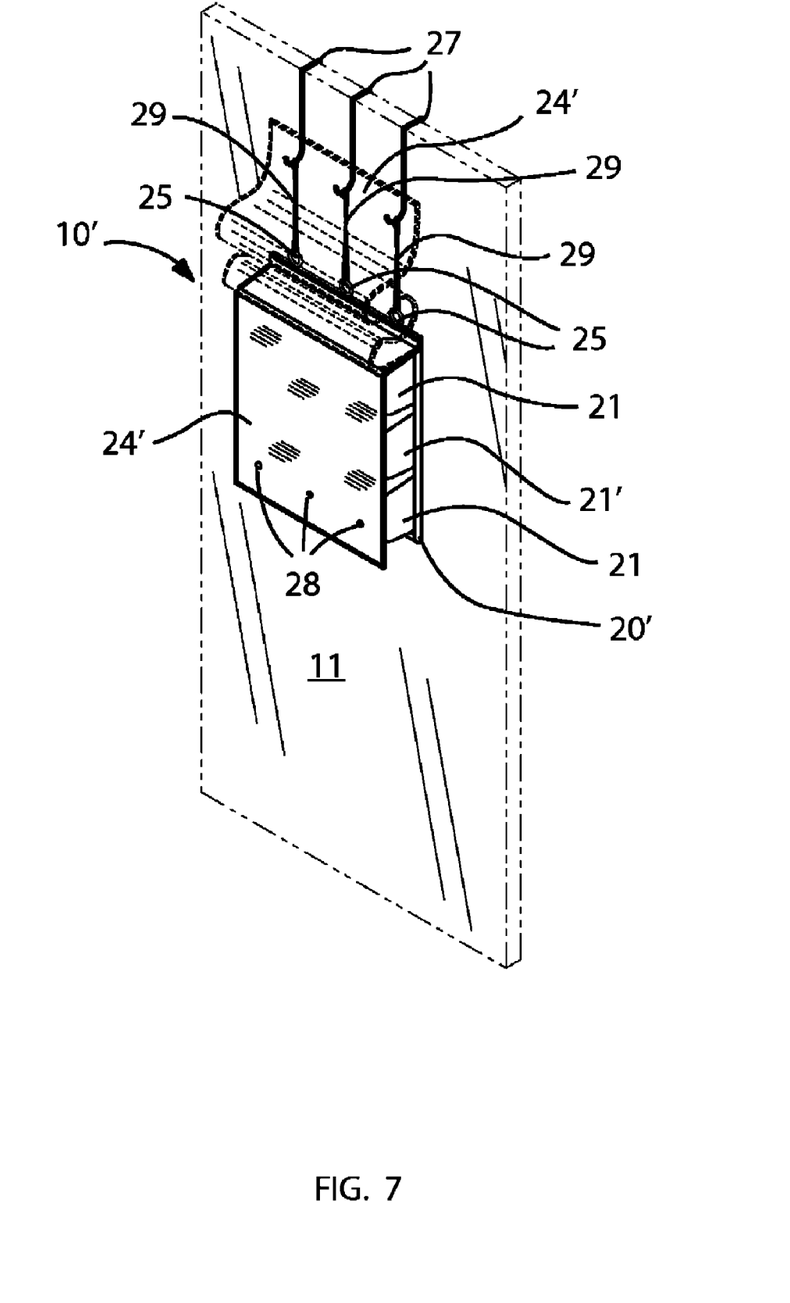
FIG. 7 is a perspective view of a storage apparatus, showing the protective shield in open and closed positions, in accordance with the embodiment shown in FIG. 4.
Figure 8:
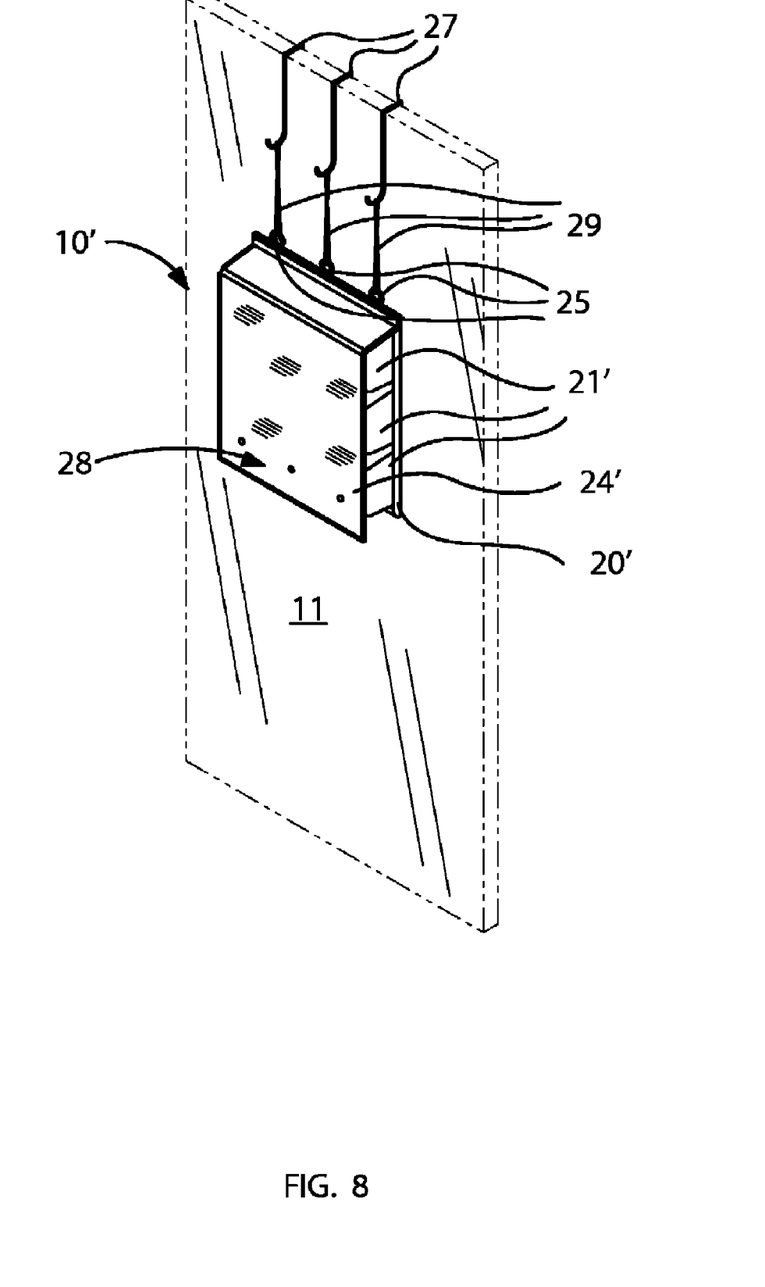
FIG. 8 is a perspective view of a storage apparatus, showing the protective shield in a closed position, in accordance with the embodiment shown in FIG. 4.
Figure 9:
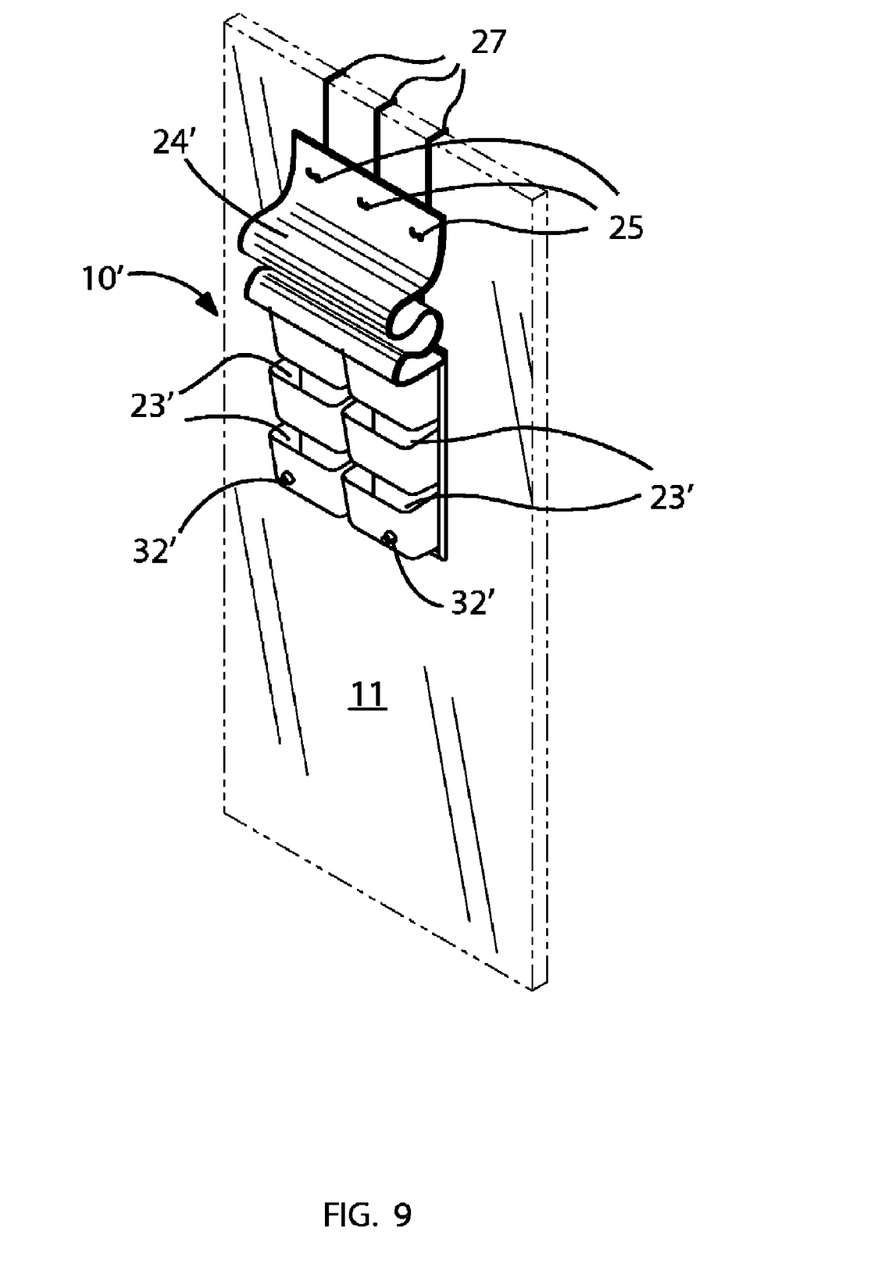
FIG. 9 is a perspective view of a storage apparatus, showing the protective shield in an open position, in accordance with the embodiment shown in FIG. 4.
Figure 10:
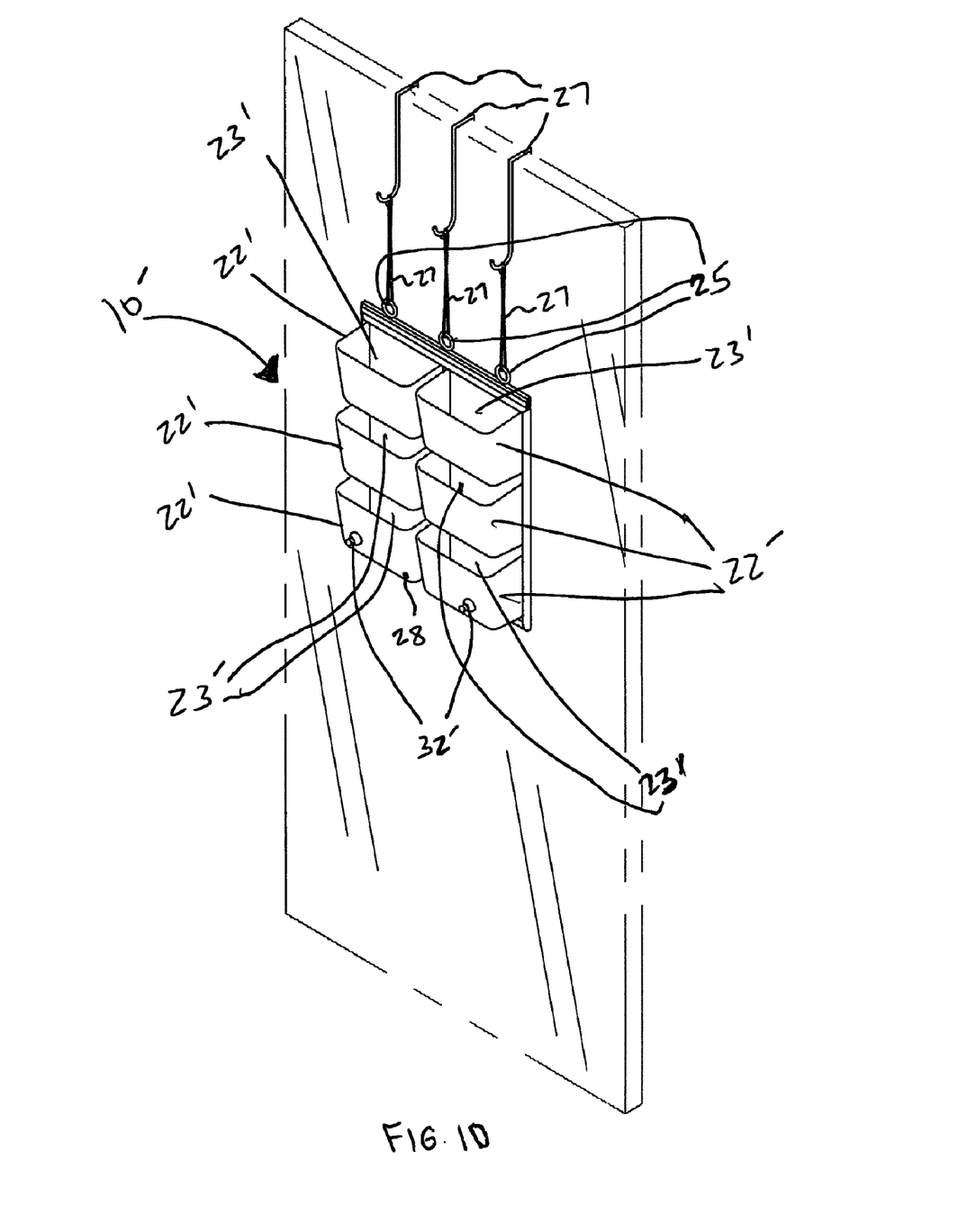
FIG. 10 is a perspective view of a storage apparatus, showing the protective shield folded behind the back wall.

Referring initially to FIGS. 1, 2 and 3, a preferred embodiment of the present invention is disclosed as including a portable storage apparatus 10 for holding hospital supplies includes a planar back wall 20 extending along an entire longitudinal length of the storage apparatus 10 and a plurality of storage compartments 21 directly affixed to an anterior surface of the back wall 20 and protruding forwardly therefrom. Each of such storage compartments 21 has a plurality of monolithically formed sides 22 defining a cavity therebetween and is provided with an open top end 23 respectively. The storage compartments 21 are provided for storing multiple supplies in an organized manner.

Referring again to FIGS. 1, 2 and 3, the apparatus 10 further includes a plurality of flexible protective shields 24 anchored to the back wall 20 and selectively adapted between raised and lowered positions which is essential such that the compartments 21 are independently exposed and isolated from an ambient region surrounding the storage apparatus 10. The protective shields 24 are freely adapted between the lowered and raised positions while the back wall 20 maintains direct contact with a door.

Each protective shield 24 covers an associated one of the storage compartments 21 and extends downwardly from the back wall 20 to a termination point defined subjacent the associated storage compartment 21. Each protective shield 24 extends along a first sloping plane registered generally orthogonal to the back wall 20 and is further seated along each of the associated storage compartments 21 respectively wherein each protective shield 24 terminates prior to reaching an adjacent one of the storage compartments 21. Each protective shield 24 further extend along a second sloping plane registered generally orthogonal to the first sloping plane while seated along an anterior face of the associated storage compartments 21 respectively. Each protective shield 24 guards the associated compartment 21 from dust and also prevents the supplies from being visible to outsiders.

Referring again to FIGS. 1, 2 and 3, the apparatus 10 further includes a mechanism 26 for hanging the storage apparatus 10 on the door which is important such that the back wall 20 contiguously lies against a planar side of the door. Such a hanging mechanism 26 includes a plurality of straps 27 removably engaged with a top most edge of the back wall 20 and extend vertically upward therefrom. Each of such straps 27 is coextensively shaped and spaced apart which is vital such that outermost ones of the straps 27 are generally vertically aligned with lateral edges of the back wall 20. The hanging mechanism 26 provides an easy method of storage, ensuring that important supplies remain within reach without taking up valuable space.

Referring again to FIGS. 1, 2 and 3, the apparatus 10 further includes a mechanism 31 for independently and simultaneously biasing each protective shield 24 to a locked position when adapted to the lowered position which is essential such that each protective shield 24 is prohibited from disengaging respective front faces of the associated storage compartments 21 when disposed at the lowered position. Such a biasing mechanism 31 includes a plurality of fasteners 32, such as VELCRO for example, coupled directly, without the use of intervening elements, to outer surfaces of each storage compartment 21 as well as an inner surface of each protective shield 24 which is important such that each protective shield 24 automatically remains statically affixed to the associated storage compartment when unrolled to the lowered position. The biasing mechanism 31 ensures that the protective shield 24 remains in a secured position.

Now referring to FIGS. 4, 5, 6, 7, 8, 9 and 10, an alternate embodiment of the present invention is disclosed as including a portable storage apparatus 10' for holding hospital supplies includes a planar back wall 20' extending along an entire longitudinal length of the storage apparatus 10' and a plurality of storage compartments 21' directly affixed to an anterior surface of the back wall 20' and protruding forwardly therefrom. Each of such storage compartments 21' has a plurality of monolithically formed sides 22' defining a cavity therebetween and is provided with an open top end 23' respectively. The storage compartments 21' are provided for storing multiple supplies in an organized manner.

Referring again to FIGS. 4, 5, 6, 7, 8, 9 and 10, the apparatus 10' further includes at least one flexible protective shield 24' anchored to the back wall 20' and selectively adapted between raised and lowered positions which is essential such that the compartments 21' are exposed and isolated from an ambient region surrounding the storage apparatus 10'. Such a protective shield 24' has a plurality of apertures 25 formed therein which adjoin a bottom most edge thereof. The protective shield 24' is freely adapted between the lowered and raised positions while the back wall 20' maintains direct contact with a door 11.

The protective shield 24' covers all of the storage compartments 21 and extends downwardly from the back wall 20' to a termination point defined subjacent a bottom-most pair of the storage compartments 21'. The protective shield 24' extends along a first sloping plane registered generally orthogonal to the back wall 20 and is further seated along selected ones of the top ends of an upper-most pair of the most storage compartments 21' respectively. The protective shield 24' further extends along a second sloping plane registered generally orthogonal to the first sloping plane while seated along an anterior face of the storage compartments 21' respectively. The protective shield 24' guards the compartments 21' from dust and also prevents the supplies from being visible to outsiders.

Referring again to FIGS. 4, 5, 6, 7, 8, 9 and 10, the apparatus 10' further includes a mechanism 26' for hanging the storage apparatus 10' on the door 11 which is important such that the back wall 20 contiguously lies against a planar side of the door 11. Such a hanging mechanism 26' includes a plurality of brackets 27 removably engaged with a top most edge of the door 11 and extending vertically down therefrom. Each of such brackets 27 is coextensively shaped and spaced apart which is vital such that outermost ones of the brackets 27 are generally vertically aligned with lateral edges of the back wall 20. A plurality of eyelets 28 is directly coupled, without the use of intervening elements, to a top most edge of the back wall 20 and juxtaposed subjacent to the brackets 27, and a plurality of flexible cords 29 have axially opposed ends anchored to the eyelets 28 and the brackets 27 respectively. Bottom hooked end portions 30 of such brackets 27 fit through the apertures 25 when the protective shield 24' is lifted to the raised position which is crucial such that the storage compartments 21' are exposed and freely acceptable by a user. The hanging mechanism 26' provides an easy method of storage, ensuring that important supplies remain within reach without taking up valuable space.

Referring again to FIGS. 4, 5, 6, 7, 8, 9 and 10, the apparatus 10' further includes a mechanism 31' for biasing the protective shield 24' to a locked position when adapted to the lowered position which is essential such that the protective shield 24' is prohibited from disengaging respective front faces of the storage compartments 21' when disposed at the lowered position. Such a biasing mechanism 31' includes a plurality of fasteners 32' coupled directly, without the use of intervening elements, to a bottom-most positioned pair of the storage compartments 21' which is important such that the aperture 25' is removably attached directly, without the use of intervening elements, to the fasteners 32' when the protective shield 24' is unrolled to the lowered position. The biasing mechanism 31' ensures that the protective shield 24' remains in a secured position.

The apparatus includes a storage device that provides ample storage space for hospital supplies and other required items, in a way that does not block doorways or impede patient/staff flow in the event of an emergency. The apparatus advantageously eliminates any potential for Life Safety Code Violations by maintaining a clear egress. The approximate, overall dimensions of the apparatus are 2 feet wide and 3 feet high, as an example. Of course, such an apparatus can be produced in a variety of sizes, as is obvious to a person of ordinary skill in the art. The apparatus is suspended by 3 place holders that are affixed temporarily to any door without damaging or marring the surface in any way, which is essential for allowing use of the apparatus in a business setting. The apparatus provides ample space to accommodate various brands of isolation equipment such as masks, gloves and gown.

The apparatus is manufactured from bacteriostatic material that is quickly wiped down and reused during quick room turnovers. Of course, such an apparatus can be manufactured from a variety of suitable materials, as is obvious to a person of ordinary skill in the art. The apparatus is covered by a bacteriostatic shield that lifts and allows easy access to the stored supplies, which is critical for care givers during busy patient care times. In addition, the shield can be closed and secured with handy restrictive devices, which is crucial for impeding residents with confusion or dementia from accessing and contaminating contents.

The present invention, as claimed, provides the unexpected and unpredictable benefit of an apparatus that is convenient and easy to use, is lightweight yet durable in design, and provides a means for convenient and space saving storage. Such an apparatus conveniently stores materials away from patient care areas and common areas, yet advantageously keeps them close at hand when needed. The apparatus hangs on a door, neatly out of the way, which is essential for allowing staff and patient traffic to effectively move about freely. The apparatus helps to eliminate citations from regulatory agencies by preventing any fire hazard. The apparatus conveniently provides ample space for needed supplies which are easily accessed as needed. The present invention can be effectively utilized in skilled nursing facilities, hospitals and other health care facilities, as well as in private homes. The apparatus is inexpensive and simple to install.

In use, a method for storing hospital supplies without blocking doorways or impeding traffic flow includes the steps of: providing a planar back wall 20 extending along an entire longitudinal length of the storage apparatus 10'; directly affixing, without the use of intervening elements, a plurality of storage compartments 21' to an anterior surface of the back wall 20' by protruding the storage compartments 21' forwardly therefrom, each of the storage compartments 21' has a plurality of monolithically formed sides 22' defining a cavity therebetween and is provided with an open top end 23' respectively; anchoring at least one flexible protective shield 24' to the back wall 20'; hanging the storage apparatus 10' on the door 11 such that the back wall 20' contiguously lays against a planar side of the door 11; and selectively adapting the protective shield 24' between raised and lowered positions while the back wall 20 maintains direct contact with a door 11 such that the compartments 21' become exposed and isolated from an ambient region surrounding the storage apparatus 10'.

In use, the method further includes the steps of: biasing the protective shield 24' to a locked position when adapted to the lowered position and thereby prohibiting the protective shield 24' from disengaging respective front faces of the storage compartments 21' why disposed at the lowered position; coupling a plurality of fasteners 32' directly, without the use of intervening elements, to a bottom-most positioned pair of the storage compartments 21'; and removably attaching the fasteners 32' directly, without the use of intervening elements, to the protective shield 24' by unrolling the protective shield 24' to the lowered position.

In use, the method further includes the steps of: covering all of the storage compartments 21' by extending the protective shield 24' downwardly from the back wall 20 to a termination point defined subjacent a bottom-most pair of the storage compartments 21'; extending the protective shield 24' along a first sloping plane registered generally orthogonal to the back wall 20 by seating the protective shield 24' along selected ones of the top ends of an upper-most pair of the most storage compartments 21' respectively; and further extending the protective shield 24' along a second sloping plane registered generally orthogonal to the first sloping plane by seating the protective shield 24' along an anterior face of the storage compartments 21' respectively.

In use, the method further includes the steps of: removably engaging a plurality of brackets 27 with a top most edge of the door 11 by vertically extending the brackets 27 down therefrom; vertically aligning outermost ones of the brackets 27 generally with lateral edges of the back wall 20; directly coupling, without the use of intervening elements, a plurality of eyelets 28 to a top most edge of the back wall 20 by juxtaposing the eyelets 28 subjacent to the brackets 27; anchoring axially opposed ends of a plurality of flexible cords 29 to the eyelets 28 and the brackets 27 respectively; and fitting bottom hooked end 30 portions of the brackets 27 through the apertures 25 by lifting the protective shield 24' to the raised position and thereby exposing the storage compartments 21' to a user.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A portable storage apparatus for holding hospital supplies without blocking doorways or impeding traffic flow, said storage apparatus comprising:

a planar back wall extending along an entire longitudinal length of said storage apparatus;

a plurality of storage compartments directly affixed to an anterior surface of said back wall and protruding forwardly therefrom, each of said storage compartments having a plurality of monolithically formed sides defining a cavity therebetween and being provided with an open top end respectively;

at least one protective shield anchored to said back wall and being selectively rolled and unrolled between raised and lowered positions such that said compartments are exposed and isolated from an ambient region surrounding said storage apparatus, said protective shield having a plurality of apertures formed therein which adjoin a bottom most edge thereof; and means for hanging said storage apparatus on a door such that said back wall contiguously lays against a planar side of the door.

2. The storage apparatus of claim 1, further comprising: means for securing said protective shield at a locked position when unrolled to the lowered position such that said protective shield is prohibited from disengaging respective front faces of said storage compartments when disposed at the lowered position.

3. The storage apparatus of claim 2, wherein said securing means comprises: a plurality of fasteners coupled directly to a bottom-most positioned pair of said storage compartments such that said apertures are removably attached directly to said fasteners when said protective shield is unrolled to the lowered position.

4. The storage apparatus of claim 1, wherein said protective shield covers all of said storage compartments and extends downwardly from said back wall to a termination point defined subjacent a bottom-most pair of said storage compartments.

5. The storage apparatus of claim 1, wherein said protective shield extends along a first sloping plane registered substantially orthogonal to said back wall and is further seated along selected ones of said top ends of an upper-most pair of said most storage compartments respectively, said protective shield further extending along a second sloping plane registered substantially orthogonal to said first sloping plane while seated along an anterior face of said storage compartments respectively.

6. The storage apparatus of claim 1, wherein said hanging means comprises:
a plurality of brackets removably engaged with a top most edge of the door and extending vertically down therefrom, each of said brackets being coextensively shaped and spaced apart such that outermost ones of said brackets are generally vertically aligned with lateral edges of said back wall;
a plurality of eyelets directly coupled to a top most edge of said back wall and juxtaposed subjacent to said brackets; and
a plurality of flexible cords having axially opposed ends anchored to said eyelets and said brackets respectively;
wherein bottom hooked end portions of said brackets fit through said apertures when said protective shield is lifted to the raised position such that said storage compartments are exposed and freely acceptable by a user.

7. A portable storage apparatus for holding hospital supplies without blocking doorways or impeding traffic flow, said storage apparatus comprising:
a planar back wall extending along an entire longitudinal length of said storage apparatus;
a plurality of storage compartments directly affixed to an anterior surface of said back wall and protruding forwardly therefrom, each of said storage compartments having a plurality of monolithically formed sides defining a cavity therebetween and being provided with an open top end respectively;
at least one flexible protective shield anchored to said back wall and being selectively rolled and unrolled between raised and lowered positions such that said compartments are exposed and isolated from an ambient region surrounding said storage apparatus, said protective shield having a plurality of apertures formed therein which adjoin a bottom most edge thereof, said protective shield being freely adapted between the lowered and raised positions while said back wall maintains direct contact with a door; and means for hanging said storage apparatus on the door such that said back wall contiguously lays against a planar side of the door.

8. The storage apparatus of claim 7, further comprising: means for securing said protective shield at a locked position when unrolled to the lowered position such that said protective shield is prohibited from disengaging respective front faces of said storage compartments when disposed at the lowered position.

9. The storage apparatus of claim 8, wherein said securing means comprises: a plurality of fasteners coupled directly to a bottom-most positioned pair of said storage compartments such that said apertures are removably attached directly to said fasteners when said protective shield is unrolled to the lowered position.

10. The storage apparatus of claim 7, wherein said protective shield covers all of said storage compartments and extends downwardly from said back wall to a termination point defined subjacent a bottom-most pair of said storage compartments.

11. The storage apparatus of claim 7, wherein said protective shield extends along a first sloping plane registered generally orthogonal to said back wall and is further seated along selected ones of said top ends of an upper-most pair of said most storage compartments respectively, said protective shield further extending along a second sloping plane registered generally orthogonal to said first sloping plane while seated along an anterior face of said storage compartments respectively.

12. The storage apparatus of claim 7, wherein said hanging means comprises:
a plurality of brackets removably engaged with a top most edge of the door and extending vertically down therefrom, each of said brackets being coextensively shaped and spaced apart such that outermost ones of said brackets are generally vertically aligned with lateral edges of said back wall;
a plurality of eyelets directly coupled to a top most edge of said back wall and juxtaposed subjacent to said brackets; and
a plurality of flexible cords having axially opposed ends anchored to said eyelets and said brackets respectively;
wherein bottom hooked end portions of said brackets fit through said apertures when said protective shield is lifted to the raised position such that said storage compartments are exposed and freely acceptable by a user.

13. A method for storing hospital supplies without blocking doorways or impeding traffic flow, said method comprising the steps of:
a. providing a planar back wall extending along an entire longitudinal length of said storage apparatus;
b. directly affixing a plurality of storage compartments to an anterior surface of said back wall by protruding said storage compartments forwardly therefrom, each of said storage compartments having a plurality of monolithically formed sides defining a cavity therebetween and being provided with an open top end respectively;
c. anchoring at least one flexible protective shield to said back wall;
d. hanging said storage apparatus on the door such that said back wall contiguously lays against a planar side of the door; and e. selectively rolling and unrolling said protective shield between raised and lowered positions while said back wall maintains direct contact with a door such that said compartments become exposed and isolated from an ambient region surrounding said storage apparatus.

14. The method of claim 13, wherein step e. comprises the step of: securing said protective shield to a locked position when unrolled to the lowered position and thereby prohibiting said protective shield from disengaging respective front faces of said storage compartments when disposed at the lowered position.

15. The method of claim 13, wherein step d. comprises the step of:
coupling a plurality of fasteners directly to a bottom-most positioned pair of said storage compartments; and
removably attaching said fasteners directly to said protective shield by unrolling said protective shield to the lowered position.

16. The method of claim 13, wherein step e. further comprises the steps of:
covering all of said storage compartments by extending said protective shield downwardly from said back wall to a termination point defined subjacent a bottom-most pair of said storage compartments.

17. The method of claim 13, wherein step e. further comprises the steps of:
extending said protective shield along a first sloping plane registered generally orthogonal to said back wall by seating said protective shield along selected ones of said top ends of an upper-most pair of said most storage compartments respectively; and
further extending said protective shield along a second sloping plane registered generally orthogonal to said first sloping plane by seating said protective shield along an anterior face of said storage compartments respectively.

18. The method of claim 13, wherein step d. comprises the steps of:
removably engaging a plurality of brackets with a top most edge of the door by vertically extending said brackets down therefrom;
vertically aligning outermost ones of said brackets generally with lateral edges of said back wall;
directly coupling a plurality of eyelets to a top most edge of said back wall by juxtaposing said eyelets subjacent to said brackets;
anchoring axially opposed ends of a plurality of flexible cords to said eyelets and said brackets respectively; and
fitting bottom hooked end portions of said brackets through said apertures by lifting said protective shield to the raised position and thereby exposing said storage compartments to a user.

* * * * *